United States Patent [19]

Toyoshima et al.

[11] Patent Number: 4,778,797

[45] Date of Patent: Oct. 18, 1988

[54] ORGANO-SILICON COMPOUNDS, PROCESS FOR THE MANUFACTURE OF SAME, AND ANTI-TUMOR AGENT COMPRISING THE COMPOUND

[75] Inventors: Shigeshi Toyoshima, Tokyo; Masayasu Kurono, Nagoya; Ryoichi Unno, Nagoya; Hiromoto Kimura, Kasugai; Koichi Ito, Tokyo, all of Japan

[73] Assignees: Sanwa Kagaku Kenkyusho Co., Ltd., Aichi; Shin-Etsu Chemical Co., Ltd., Tokyo, both of Japan

[21] Appl. No.: 773,967

[22] Filed: Sep. 9, 1985

[30] Foreign Application Priority Data

Sep. 10, 1984 [JP] Japan .................. 59-188197

[51] Int. Cl.$^4$ .................. C07F 7/10; A61K 31/695
[52] U.S. Cl. .................. 514/274; 544/229
[58] Field of Search .................. 544/229; 514/274

[56] References Cited

U.S. PATENT DOCUMENTS 4,478,839 10/1984 Benneche et al. .................. 514/274

FOREIGN PATENT DOCUMENTS 56-63966 5/1981 Japan .
57-38789 3/1982 Japan .
59-98091 6/1984 Japan .................. 544/229
59-122430 7/1984 Japan .................. 544/229

*Primary Examiner*—Robert Gerstl
*Attorney, Agent, or Firm*—Armstrong, Nikaido, Marmelstein & Kubovcik

[57] ABSTRACT

Novel organo-silicone compounds represented by the formula,

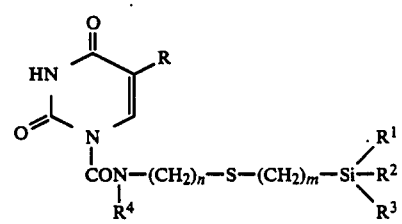

wherein R is hydrogen, halogen or alkyl group, $R^1$, $R^2$ and $R^3$ are alkyl group, alkoxy group, phenyl radical, substituted phenyl radical, alkylcarbonyloxy group, or trialkylsilyloxy group, respectively, $R^4$ is hydrogen, alkyl or alkenyl grup, and m and n are an integer, respectively but those do not represent same integer of 2, when all of $R^1$, $R^2$ and $R^3$ represents methyl radical, a process for the manufacture of the compounds, and an anti-tumor agent which comprises as an effective component, at least one of the compounds.

38 Claims, No Drawings

ORGANO-SILICON COMPOUNDS, PROCESS FOR THE MANUFACTURE OF SAME, AND ANTI-TUMOR AGENT COMPRISING THE COMPOUND

FIELD OF THE INVENTION

The present invention relates to novel organo-silicone compounds, a process for the manufacture of same, and an anti-tumor agent which comprises as an effective component, at least one of the compounds.

RELATED ARTS

As silicon-containing compounds having a pharmaceutical activity of anti-tumor action, so-called "Silatorane Compounds" have been known, but these compounds have a disadvantage in actual or clinical use, in view of its high toxicity.

There is a compound of 5-fluorouracil which has actually and clinically employed as one of anti-tumor agents. This compound has an excellent anti-tumor action but shows in oral dosage a higher toxicity of that it often causes a certain trouble in digestive canals and thus this compound has exclusively been dosed through an injection route. In order to overcome this disadvantage, namely for making an oral dosage possible, 1-(2-tetrahydrofuryl)-5-fluorouracil has been developed. This compound shows a lower toxicity in oral dosage thereof, but has a disadvantage in that an anti-tumor activity thereof is low.

Meanwhile, in Jap. Unexamined Pat. Appln. Gazette Nos. 63 966/1981 and 38 789/1982, there are disclosed 1-[2-(2-trimethylsilylethyl)thio]ethylcarbamoyl]-5-fluorouracil and 2-[2-aminoethylthio)]ethyltrimethylsilane, respectively. These compounds have a higher anti-tumor activity but there are some doubt in an actual use thereof, since each has a higher toxicity similar to the Silatorane compounds and shows an undesirable side-reaction.

SUMMARY OF THE INVENTION

An object of the invention is to provide novel organo-silicone compounds, each having a higher anti-tumor activity and showing no or lower toxicity, particularly in oral dosage, whereby such a conflicting problem between a level on anti-tumor activity and a safety in actual use, which have been encountered in the prior anti-tumor agents, can be dissolved.

According to the invention, said and other objects to be appreciated by fully understanding the invention can be attained by a novel organo-silicone compound represented by the formula,

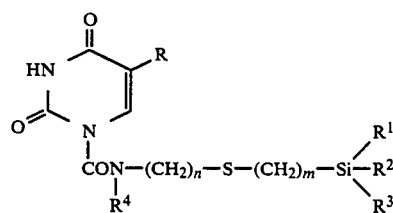

(I)

wherein R is hydrogen, halogen or alkyl group, $R^1$, $R^2$ and $R^3$ are alkyl group, alkoxy group, phenyl radical, substituted phenyl radical, alkylcarbonyloxy group or trialkylsilyloxy group, respectively, $R^4$ is hydrogen, alkyl or alkenyl group, and m and n are an integer, respectively but those do not represent same integer of 2, when all of $R^1$, $R^2$ and $R^3$ represents methyl radical. Namely, each of the compounds shown by said Formula I shows an excellent anti-tumor activity and a quite low toxicity.

In the compounds shown by the Formula I, the term "halogen" means any of fluorine, chlorine, bromine and iodine but fluorine is most preferable. The alkyl group may be of straight-chain alkyl radicals, branched-chain alkyl radicals or cycloalkyl radicals. As examples for the straight-chain alkyl radicals, one having 1 to 10 carbon atoms, for instance methyl, ethyl, n-propyl, n-butyl, n-pentyl, n-hexyl, n-decyl and the like may be listed. As examples for the the branched-chain alkyl radicals, isopropyl, isobutyl, s-butyl, t-butyl, isopentyl and the like radicals may be listed. As examples for the cycloalkyl radicals, one having 3 or more carbon atoms, for instance cyclopropyl, cyclobutyl, cyclopentyl, cyclohexyl, cycloheptyl and the like radicals may be listed. As the alkoxy group, methoxy, ethoxy, 2-methoxyethoxy and the like radicals may be listed. As substituents for the substituted phenyl radical, p-chloro, p-bromo, p-methyl, p-methoxy and the like may be listed. As the alkylcarbonyloxy group, acetoxy, propionyloxy and the like radicals may be listed. As the trialkylsilyloxy group, trimethylsilyloxy, triethylsilyloxy and the like radicals may be listed. As the alkenyl group, vinyl, allyl, isopropenyl and the like radicals may be listed.

According to a method of the invention, the compound as shown by the Formula I, can basically be prepared by reacting a compound represented by the formula.

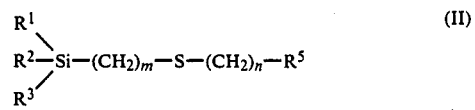

(II)

wherein $R^1$, $R^2$, $R^3$, m and n have the meaning referred to, and $R^5$ is a radical of $-N=C=O$, $-NHR^4$ or $-NR^4-CO-Cl$, in which $R^4$ has the meaning referred to, with a compound represented by the formula,

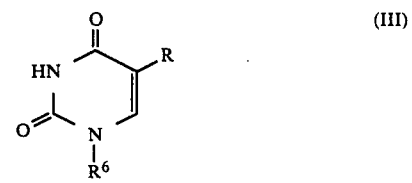

(III)

wherein R has the meaning referred to, and $R^6$ is hydrogen, alkali metal or a radical of $-COCl$.

Referring to in more detail, the compound as shown by the Formula I can be prepared in accordance with one of the following methods.

(A) A method, in which a compound represented by the formula,

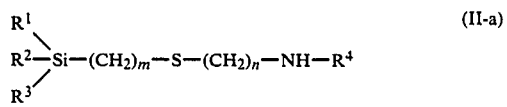

(II-a)

wherein $R^1$, $R^2$, $R^3$, $R^4$, m and n have the meaning referred to, is reacted with 1-chloroformyl-5-substituted uracil represented by the formula,

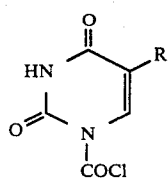

(III-a)

wherein R has the meaning referred to.

This reaction proceeds with by merely stirring the both raw materials in an equimolar amount, in the presence of a solvent. As the solvent, pyridine, N,N-dimethylformamide, N,N-dimethylacetamide, dimethylsulfoxide, hexamethylphosphoric triamide, acetonitrile, nitromethane and the like may be used. A reaction temperature depends on kinds of the raw materials and solvent and thus it is not always in a constant level but a temperature in a range of 0° to 10° C. is preferable, since said chloroformyl compound shown by the Formula III-a is, in general, not so stable.

The starting material of 1-chloroformyl-5-fluorouracil can be synthesized according to the method as disclosed in "Bull. Chem. Soc. Japan", Vol. 50, No. 9, Pages 2406 to 2412 (1977).

(B) A method, in which a compound represented by the formula

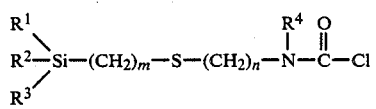

(II-b)

wherein $R^1$, $R^2$, $R^3$, $R^4$, m and n have the meaning referred to, is reacted with 5-substituted uracil represented by the formula,

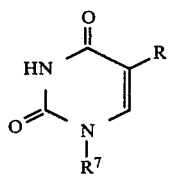

(III-b)

wherein R has the meaning referred to, and $R^7$ is hydrogen or alkali metal.

This reaction also proceeds with by merely stirring the both raw materials in an equimolar amount, in the presence of a solvent. As the solvent, those referred to on the Method (A) may be employed. The reaction temperature depends on kinds of the raw materials and solvent but, in general, 0° to 50° C. is preferable.

The raw material shown by the Formula II-b can be prepared by reacting the compound shown by the Formula II-a with phosgene in an equimolar amount. In general, the reaction can conveniently proceed with by using a base in the presence of a solvent. As the base, triethylamine, pyridine, potassium carbonate or the like may be used. As the solvent, carbon tetrachloride or the like halogenated carbons, ethyl ether, tetrahydrofuran, dioxane or the like ethers, benzene, toluene, xylene or the like aromatic hydrocarbons may be employed. The reaction temperature depends on kinds of the raw material and solvent and thus it is not always in a constant level but, in general, a temperature of 0° to 20° C. is selected. The resulting carbamoylchloride shown by the Formula II-b can be used for the reaction with the compound shown by the Formula III-b, without any purifying procedure.

(C) The compounds shown by the Formula I, wherein $R^4$ is hydrogen, namely those represented by the formula,

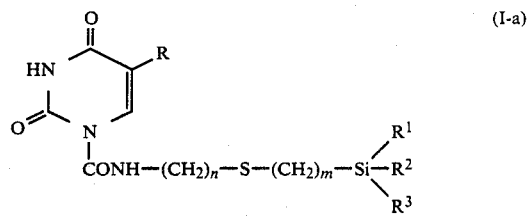

(I-a)

wherein R, $R^1$, $R^2$, $R^3$, m and n have the meaning referred to, can also be prepared by reacting an isocyanate represented by the formula,

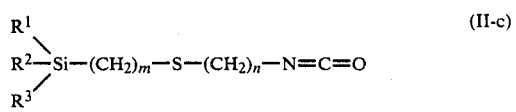

(II-c)

wherein $R^1$, $R^2$, $R^3$, m and n have the meaning referred to, with 5-substituted uracil represented by the formula,

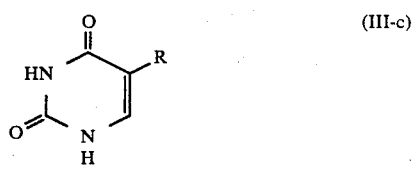

(III-c)

wherein R has the meaning referred to.

This reaction also proceeds with by merely stirring the both raw materials in an equimolar amount, in the presence of a solvent. As the solvent, those referred to on the Method (A) can be employed. The reaction temperature depends on kinds of the raw materials and solvent and thus it is not always in a constant level but, in general, a temperature of 0° to 100° C. is selected.

The raw material shown by the Formula II-c can be prepared by reacting the compound shown by the Formula II-a with phosgene in 1.0 to 3.0 times molar amount. This reaction, in general, proceeds with by merely stirring the reactants in the presence of a solvent. As the solvent, benzene, toluene, xylene or the like aromatic hydrocarbon can be employed. The reaction temperature depends on kinds of the raw material and solvent but a temperature of 0° C. to a boiling point of the solvent is usually selected.

EFFECT OF THE INVENTION

Novel organo-silicone compounds according to the invention has an anti-tumor activity and more particularly an inhibiting action to various solid tumors and shows no or quite low toxicity in both of oral and non-oral dosage thereof. Therefore, it can be used as a safety effective component for anti-tumor agents.

FORM AND DOSING AMOUNT

Each of the compounds according to the invention can be dosed in both of oral and non-oral routes. For the oral dosage, the compound may be made with conventional additives or carriers into a tablet, capsule, granule or other form. For the non-oral dosage, the compound may be made with conventional additives or carriers into an injection, suppository or the like form.

A dosing amount of the compound for human depends on kind of the compound to be used, condition of illness, age of a patient, form of the medicine and other factors but in case for an adult, 300 to 5000 mg/day on oral dosage and 100 to 2000 mg/day on suppository are preferable.

DETAILED DESCRIPTION OF PREFERRED EMBODIMENTS

The invention will now be explained with reference to Examples and Pharmaceutical Test Examples.

EXAMPLE 1

5-Fluoro-3,4-dihydro-2,4-dioxo-N-[2-[[3-(trimethylsilyl)propyl]thio]ethyl]-1(2H)-pyrimidinecarboxamide Trichloromethyl chloroformate (9.90 g, 50.0 mmol) was added dropwise with stirring to a mixture of 5-fluoro-2,4(1H,3H)-pyrimidinedione (13.0 g, 0.100 mol) and active carbon (3.0 g) in 400 ml of dry pyridine, while the temperature was maintained at 5° C.

After stirring for one hour, the unreactive phosgene was removed in vacuo at 5° C.

Then, to the reaction mixture 2-[[3-(trimethylsilyl)propyl]thio]ethyl amine (9.57 g, 50.0 mmol) was added dropwise at 10° C. under argon atmosphere, and stirred for one hour. The reaction mixture was evaporated to dryness in vacuo, the resulting residue was dissolved in ethyl acetate (400 ml) and then the active carbon was filtered off, the filtrate was washed with 3% hydrochloric acid (300 ml) and then with warm (500 ml). The organic phase was dried over sodium sulfate and the solvent was evaporated to dryness in vacuo.

The crude crystalline was recrystalized from ethyl ether to yield the desired compound (15.7 g, 90.7%).

Melting point: 109°–110° C.

Elementary analysis: $C_{13}H_{22}FN_3O_3SSi$. Cal.: C, 44.94; H, 6.38; N, 12.09. Found: C, 44.75; H, 6.47; N, 11.99.

IR ($\nu_{max}^{KBr}$) cm$^{-1}$: 3300 ($\nu_{NH}$), 2960, 2920($\nu_{CH}$), 1740, 1700($\nu_{C=O}$), 1525($\delta_{NH}$), 1250 ($\nu_{C-Si}$)

$^1$H-NMR (CDCl$_3$) δppm:

| | |
|---|---|
| 0.03 | (9H, s, —Si(CH$_3$)$_3$) |
| 0.83 | 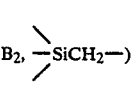 (2H, A$_2$B$_2$, \Si-CH$_2$—) |
| 1.60 |  (2H, m, \SiCH$_2$C$\underline{H}_2$CH$_2$S—) |
| 2.58 |  (2H, t, J=7.6Hz, \SiCH$_2$CH$_2$C$\underline{H}_2$S—) |
| 2.74 | (2H, t, J=6.4Hz, —SC$\underline{H}_2$CH$_2$NH—) |
| 3.61 | (2H, q, J=6.4Hz, —SCH$_2$C$\underline{H}_2$NH—) |
| 7.44 | (1H, d, J=7.0Hz, C$_6$—H) |
| 9.00–9.60 | (2H, m, N$_3$—H, N$_8$—H) |

MS (EI/DI) m/z: 347 (M+), 332, 202, 73(base peak).

EXAMPLE 2

5-Fluoro-3,4-dihydro-2,4-dioxo-N-[2-[[(2-triethylsilyl)ethyl]thio]ethyl]-1(2H)-pyrimidinecarboxamide This compound was prepared by the similar procedure as in the case of Example 1, except for the treatment with 2-[[2-(triethylsilyl)ethyl]thio]ethyl amine (11.0 g, 50.0 mmol) instead of 2-[[3-(trimethylsilyl)propyl]thio]ethyl amine. The crude material was recrystalized from ethyl ether to yield the desired compound (17.5 g, 93.2%).

Melting point: 76° C.

Elementary analysis: $C_{15}H_{26}FN_3O_3SSi$. Cal.: C, 47.97; H, 6.98; N, 11.19. Found: C, 47.67; H, 7.22; N, 11.17.

IR ($\nu_{max}^{KBr}$) cm$^{-1}$: 3320($\nu_{NH}$), 2950($\nu_{CH}$), 1740, 1700($\nu_{C=O}$), 1525($\delta_{NH}$), 1230($\nu_{C-Si}$).

$^1$H-NMR (CDCl$_3$) δppm:

| | |
|---|---|
| 0.27–1.36 | (17H, m, —CH$_2$Si(C$_2$H$_5$)$_3$) |
| 2.54 | 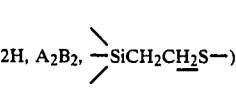 (2H, A$_2$B$_2$, \SiCH$_2$C$\underline{H}_2$S—) |
| 2.74 | (2H, t, J=7.0Hz, —SC$\underline{H}_2$CH$_2$NH—) |
| 3.58 | (2H, q, J=7.0Hz, —SCH$_2$C$\underline{H}_2$NH—) |
| 8.23 | (1H, m, N$_3$—H) |
| 8.42 | (1H, d, J=7.0Hz, C$_6$—H) |
| 9.23 | (1H, m, N$_8$—H) |

MS (EI/DI) m/z: 216, 188(base peak).

EXAMPLE 3

N-[2-[[2-(Dimethylphenylsilyl)ethyl]thio]ethyl]-5-fluoro-3,4-dihydro-2,4-dioxo-1(2H)-pyrimidinecarboxamide This compound was prepared by the similar procedure as in the case of Example 1, except for treatment with 2-[[2-(dimethylphenylsilyl)ethyl]thio]ethyl amine (10.8 g, 45.0 mmol) instead of 2-[[3-trimethylsilyl)propyl]thio]ethyl amine. The crude material was recrystalized from ethyl ether to yield the desired compound (15.5 g, 87.3%).

Melting point: 90°–91° C.

Elementary analysis: $C_{15}H_{26}FN_3O_3SSi$. Cal.: C, 51.62; H, 5.61; N, 10.62. Found: C, 51.66; H, 5.71; N, 10.54.

IR ($\nu_{max}^{KBr}$) cm$^{-1}$: 3350, 3310 ($\nu_{NH}$), 2960, 2930($\nu_{CH}$), 1735($\nu_{C=O}$), 1505($\delta_{NH}$).

| | |
|---|---|
| 0.27 | (6H, s, —Si(C$\underline{H}_3$)$_2$Ph) |
| 1.10 | 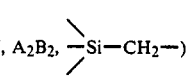 (2H, A$_2$B$_2$, \Si—CH$_2$—) |

-continued

| 2.49 | 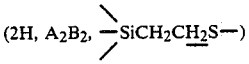 (2H, A₂B₂, $-\text{SiCH}_2\underline{\text{CH}_2}\text{S}-$) |
| --- | --- |
| 2.69 | (2H, t, J=6.0Hz, $-\text{SCH}_2\underline{\text{CH}_2}\text{N}-$) |
| 3.52 | (2H, q, J=6.0Hz, $-\text{SCH}_2\underline{\text{CH}_2}\text{N}-$) |
| 7.33 | (5H, m, $-\text{S(CH}_3)_2\underline{\text{Ph}}$) |
| 8.40 | (1H, d, J=7.0Hz, $\text{C}_6-\text{H}$) |
| 9.25 | (2H, m, $\text{N}_3-\text{H}, \text{N}_8-\text{H}$) |

FD-MS m/z: 395(M+, base peak).

EXAMPLE 4

N-[2-[[2-(Dimethyloctylsilyl)ethyl]thio]ethyl]-5-fluoro-3,4-dihydro-2,4-dioxo-1(2H)-pyrimidinecarboxamide This compound was prepared by the similar procedure as in the case of Example 1, except for treatment with 2-[[2-(dimethyloctylsilyl)ethyl]thio]ethyl amine (13.8 g, 50.0 mmol) instead of 2-[[3-(trimethylsilyl)propyl]thio]ethyl amine. The crude material was recrystalized from ethyl ether-n-hexane to yield the desired compound (17.1 g, 79.1%).

Melting point: 60°–61° C.

Elementary analysis: $\text{C}_{19}\text{H}_{31}\text{FN}_3\text{O}_3\text{SSi}$. Cal.: C, 52,87; H, 7.94; N, 9.74. Found: C, 52.63; H, 8.26; N, 9.71.

IR ($\nu_{max}^{KBr}$) cm$^{-1}$: 3430($\nu_{NH}$), 2930, 2860($\nu_{CH}$), 1735($\nu_{C=O}$), 1530($\delta_{NH}$).

$^1$H-NMR (CDCl₃) δppm:

| -0.05 | (6H, s, $-\text{Si(CH}_3)_2$) |
| --- | --- |
| 0.22–1.52 | (19H, m, $-\text{CH}_2\text{Si(CH}_2)_7\text{CH}_3$) |
| 2.46 | 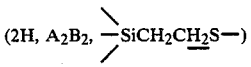 (2H, A₂B₂, $-\text{SiCH}_2\underline{\text{CH}_2}\text{S}-$) |
| 2.72 | (2H, t, J=6.0Hz, $-\text{SCH}_2\underline{\text{CH}_2}\text{NH}-$) |
| 3.57 | (2H, q, J=6.0Hz, $-\text{SCH}_2\underline{\text{CH}_2}\text{NH}-$) |
| 8.42 | (1H, d, J=7.0Hz, $\text{C}_6-\text{H}$) |
| 9.27 | (2H, m, $\text{N}_3-\text{H}, \text{N}_8-\text{H}$) |

MS (EI/DI) m/z: 188, 160(base peak)

EXAMPLE 5

5-Fluoro-3,4-dihydro-N-[2-[[2-(isopropyldimethylsilyl)ethyl]thio]ethyl]-2,4-dioxo-1(2H)-pyrimidinecarboxamide This compound was prepared by the similar procedureas in the case of Example 1, except for treatment with 2-[[2-(isopropyldimethylsilyl)ethyl]thio]ethyl amine (10.3 g, 50.0 mmol) instead of 2-[[3-(trimethylsilyl)propyl]thio]ethyl amine. The crude material was recrystalized from ethyl ether-n-hexane to yield the desired compound (16.8 g, 93.0%).

Melting point: 85°–86° C.

Elementary analysis: $\text{C}_{14}\text{H}_{24}\text{FN}_3\text{O}_3\text{SSi}$. Cal.: C, 46.51; H, 6.69; N, 11.62. Found: C, 46.34; H, 6.87; N, 11.63.

IR ($\nu_{max}^{KBr}$) cm$^{-1}$: 3420($\nu_{NH}$), 2960($\nu_{CH}$), 1725, 1690($\nu_{C=O}$), 1525($\delta_{NH}$), 1250($\nu_{C-Si}$).

$^1$N-NMR (CDCl₃) δppm:

| -0.06 | (6H, s, $-\text{Si(CH}_3)_2$) |
| --- | --- |
| 0.32–1.15 | (9H, m, $-\text{CH}_2\text{SiCH(CH}_3)_2$) |
| 2.12–3.09 | 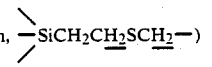 (4H, m, $-\text{SiCH}_2\underline{\text{CH}_2}\text{S}\underline{\text{CH}_2}-$) |
| 3.57 | (2H, q, J=6.0Hz, $-\text{SCH}_2\underline{\text{CH}_2}\text{NH}-$) |
| 8.42 | (1H, d, J=7.0Hz, $\text{C}_6-\text{H}$) |
| 9.30 | (2H, m, $\text{N}_3-\text{H}, \text{N}_8-\text{H}$) |

FD-MS m/z: 361(M+), 318(base peak).

EXAMPLE 6

N-[2-[[2-(Butyldimethylsilyl)ethyl]thio]ethyl]-5-fluoro-3,4-dihydro-2,4-dioxo-1(2H)-pyrimidinecarboxamide This compound was prepared by the similar procedure as in the case of Example 1, except for treatment with 2-[[2-(butyldimethylsilyl)ethyl]thio]ethyl amine (11.0 g, 50.0 mmol) instead of 2-[[3-(trimethylsilyl)propyl]thio]ethyl amine. The crude material was recrystalized from methanol to yield the desired compound (17.2 g, 91.5%).

Melting point: 71°–72° C.

Elementary analysis: $\text{C}_{15}\text{H}_{26}\text{FN}_3\text{O}_3\text{SSi}$. Cal.: C, 47.98; H, 6.98; N, 11.19. Found: C, 47.63; H, 7.14; N, 11.14.

IR ($\nu_{max}^{KBr}$) cm$^{-1}$: 3300($\nu_{NH}$), 2960, 2920($\nu_{CH}$), 1735($\nu_{C=O}$), 1520($\delta_{NH}$), 1250($\nu_{C-Si}$).

$^1$H-NMR (CDCl₃) δppm:

| -0.04 | (6H, s, $-\text{Si(CH}_3)_2$) |
| --- | --- |
| 0.16–1.62 | (11H, m, $-\text{CH}_2\text{Si(CH}_2)_3\text{CH}_3$) |
| 2.26–3.19 |  (4H, m, $-\text{SiCH}_2\underline{\text{CH}_2}\text{S}\underline{\text{CH}_2}-$) |
| 3.39–3.82 | (2H, m, $-\text{SCH}_2\underline{\text{CH}_2}\text{NH}-$) |
| 8.42 | (1H, d, J=6.0Hz, $\text{C}_6-\text{H}$) |
| 9.21 | (2H, m, $\text{N}_3-\text{H}, \text{N}_8-\text{H}$) |

FAB-MS m/z: 376[(M+1)+].

Example 7

5-Fluoro-3,4-dihydro-N-[2-[[2-(methyldiphenylsilyl)ethyl]thio]ethyl]-2,4-dioxo-1(2H)-pyrimidinecarboxamide This compound was prepared by the similar procedure as in the case of Example 1, except for treatment with 2-[[2-(methyldiphenylsilyl)ethyl]thio]ethyl amine (12.0 g, 40.0 mmol) instead of 2-[[3-(trimethylsilyl)propyl]thio]ethyl amine. The crude material was recrystalized from methanol to yield the desired compound (12.6 g, 69.0%).

Melting point: 119°–120° C.

Elementary analysis: $\text{C}_{22}\text{H}_{24}\text{FN}_3\text{O}_3\text{SSi}$. Cal.: C, 57.75; H, 5.29; N, 9.18. Found: C, 57.51; H, 5.32; N, 9.06.

IR ($\nu_{max}^{KBr}$) cm$^{-1}$: 3430($\nu_{NH}$), 2840($\nu_{CH}$), 1740($\nu_{C=O}$), 1520($\delta_{NH}$), 1235($\nu_{C-Si}$).

$^1$H-NMR (CDCl₃) δppm:

| | |
|---|---|
| 0.50 | (3H, s, Ph₂CH₃Si—) |
| 1.34 | (2H, A₂B₂, \\SiCH₂—/) |
| 2.50 | (2H, A₂B₂, \\SiCH₂CH₂S—/) |
| 2.63 | (2H, t, J=6.0Hz, —SCH₂CH₂NH—) |
| 3.45 | (2H, q, J=6.0Hz, —SCH₂CH₂NH—) |
| 7.28 | (10H, m, Ph₂CH₃Si—) |
| 8.34 | (1H, d, J=6.0Hz, C₆—H) |
| 9.17 | (2H, m, N₃—H, N₈—H) |

MS (EI/DI) m/z: 327, 285, 197(base peak).

Example 8

5-Fluoro-3,4-dihydro-2,4-dioxo-N-[3-[[2-(trimethylsilyl)ethyl]thio]propyl]-1-(2H)-pyrimidinecarboxamide This compound was prepared by the similar procedure as in the case of Example 1, except for treatment with 3-[[2-(trimethylsilyl)ethyl]thio]propyl amine (9.55 g, 50.0 mmol) instead of 2-[[3-(trimethylsilyl)propyl]thio]ethyl amine. The crude material was recrystalized from ethyl ether-n-hexane to yield the desired compound (13.3 g, 76.4%).

Melting point: 114°–115° C.

Elementary analysis: $C_{13}H_{22}FN_3O_3SSi$. Cal.: C, 44.94; H, 6.38; N, 12.09. Found: C, 44.87; H, 6.55; N, 12.11.

IR $(\nu_{max}^{KBr})$ cm⁻¹: 3330($\nu_{NH}$), 2960($\nu_{CH}$), 1740($\nu_{C=O}$), 1505($\delta_{NH}$), 1250($\nu$C-Si).

¹H-NMR (CDCl₃) δppm:

| | |
|---|---|
| 0.03 | (9H, s, (CH₃)₃Si—) |
| 0.81 | (2H, A₂B₂, \\SiCH₂—/) |
| 1.87 | (2H, m, —SCH₂CH₂CH₂NH—) |
| 2.21–2.94 | (4H, m, \\SiCH₂CH₂SCH₂/) |
| 3.49 | (2H, q, J=6.0Hz, CH₂NH—) |
| 8.42 | (1H, d, J=7.0Hz, C₆—H) |
| 9.10 | (1H, m, N₃—H) |
| 9.50 | (1H, m, N₈—H) |

MS (EI/DI) m/z: 347(M+), 305, 73(base peak).

Example 9

5-Fluoro-3,4-dihydro-N-[3-[[2-(isopropyldimethylsilyl)ethyl]thio]propyl]-2,4-dioxo-1(2H)-pyrimidinecarboxamide This compound was prepared by the similar procedure as in the case of Example 1, except for treatment with 3-[[2-(isopropyldimethylsilyl)ethyl]thio]propyl amine (11.0 g, 50.0 mmol) instead of 1-[[3-(trimethylsilyl)propyl]thio]ethyl amine. The crude material was recrystalized from ethyl ether to yield the desired compound (17.3 g, 92.0%).

Melting point: 122°–123° C.

Elementary analysis: $C_{15}H_{26}FN_3O_3SSi$. Cal.: C, 47.98; H, 6.98; N, 11.19. Found: C, 48.16; H, 7.10; N, 11.40.

IR $(\nu_{max}^{KBr})$ cm⁻¹: 3330($\nu_{NH}$), 2950($\nu_{CH}$), 1735, 1660($\nu_{C=O}$), 1250($\nu$C-Si).

¹H-NMR (CDCl₃) δppm:

| | |
|---|---|
| −0.03 | (6H, s, —Si(CH₃)₂) |
| 0.58–1.11 | (9H, m, —CH₂SiCH(CH₃)₂) |
| 1.89 | (2H, q, J=7.0Hz, —SCH₂CH₂CH₂NH—) |
| 2.35–2.78 | (4H, m, —CH₂SCH₂—) |
| 3.53 | (2H, q, J=6.5Hz, —CH₂NH—) |
| 8.46 | (1H, d, J=7.0Hz, C₆—H) |
| 9.05 | (2H, m, N₃—H, N₈—H) |

FD-MS m/z: 375(M+), 332(base peak).

Example 10

5-Fluoro-3,4-dihydro-2,4-dioxo-N-[3-[[3-(trimethylsilyl)propyl]thio]propyl]-1(2H)-pyrimidinecarboxamide This compound was prepared by the similar procedure as in the case of Example 1, except for treatment with 3-[[3-(trimethylsilyl)propyl]thio]propyl amine (10.3 g, 50.0 mmol) instead of 2-[[3-(trimethylsilyl)propyl]thio]ethyl amine. The crude material was recrystalized from ethyl ether-n-hexane to yield the desired compound (16.6 g, 92.0%).

Melting point: 105°–106° C.

Elementary analysis: $C_{14}H_{24}FN_3O_3SSi$. Cal.: C, 46.51; H, 6.69; N, 11.62. Found: C, 46.80; H, 6.71; N, 11.74.

IR $(\nu_{max}^{KBr})$ cm⁻¹: 3330($\nu_{NH}$), 2960($\nu_{CH}$), 1735, 1670($\nu_{C=O}$), 1250($\nu$C-Si).

¹H-NMR (CDCl₃) δppm:

| | |
|---|---|
| −0.02 | (9H, s, (CH₃)₃Si—) |
| 0.42–0.75 | (2H, m, \\SiCH₂—/) |
| 1.22–2.15 | (4H, m, —CH₂CH₂SCH₂CH₂CH₂NH—) |
| 2.32–2.75 | (4H, m, —CH₂SCH₂—) |
| 3.52 | (2H, q, J=6.5Hz, —CH₂NH—) |
| 8.45 | (1H, d, J=7.0Hz, C₆—H) |
| 9.05 | (1H, m, N₃—H) |
| 9.45 | (1H, m, N₈—H) |

FD-MS m/z: 361(M+), 73(base peak).

Example 11

5-Fluoro-3,4-dihydro-N-[3-[[3-(isopropyldimethylsilyl)-propyl]thio]propyl]-2,4-dioxo-1(2H)-pyrimidinecarboxamide This compound was prepared by the similar procedure as in the case of Example 1, except for treatment with 3-[[3-(isopropyldimethylsilyl)propyl]thio]propyl amine (11.7 g, 50.0 mmol) instead of 2-[[3-(trimethylsilyl)propyl]thio]ethyl amine. The crude material was recrystalized from ethyl ether-n-hexane to yield the desired compound (16.4 g, 84.3%).

Melting point: 101°–102° C.

Elementary analysis: $C_{16}H_{28}FN_3O_3SSi$. Cal.: C, 49.33; H, 7.24; N, 10.79. Found: C, 49.52; H, 7.10; N, 10.60.

IR $(\nu_{max}^{KBr})$ cm$^{-1}$: 3330($\nu_{NH}$), 2950($\nu_{CH}$), 1720($\nu_{C=O}$), 1670($\nu_{CONH}$).

$^1$H-NMR (CDCl$_3$) δppm:

−0.03    (6H, s, (CH$_3$)$_2$Si—)

0.19–1.15 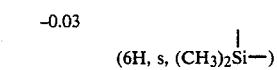
(8H, m, (C<u>H</u>$_3$)$_2$—CH—Si—C<u>H</u>$_2$—)

1.25–2.25 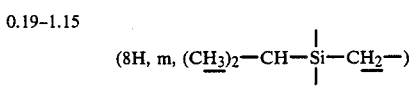
(5H, m, (CH$_3$)$_2$C<u>H</u>—SiCH$_2$C<u>H</u>$_2$CH$_2$—SCH$_2$C<u>H</u>$_2$—)

2.35–2.75    (4H, m, —CH$_2$SCH$_2$—)

3.54    (2H, q, J=6.0Hz, —NHC<u>H</u>$_2$—)

8.46    (1H, d, J=7.0Hz, C$_6$—H)
9.05    (2H, br., 2 × NH)

FD-MS m/z: 346(base peak)

Example 12

5-Fluoro-3,4-dihydro-N-[2-[[3-(isopropyldimethylsilyl)-propyl]thio]ethyl]-2,4-dioxo-1(2H)-pyrimidinecarboxamide This compound was prepared by the similar procedure as in the case of Example 1, except for treatment with 2-[[3-(isopropyldimethylsilyl)propyl]thio]ethyl amine (11.0 g, 50.0 mmol) instead of 2-[[3-(trimethylsilyl)propyl]thio]ethyl amine. The crude material was recrystalized from ethyl ether to yield the desired compound (16.7 g, 89.0%).

Melting point: 113°–114° C.

Elementary analysis: $C_{15}H_{26}FN_3O_3SSi$. Cal.: C, 47.98; H, 6.98; N, 11.19. Found: C, 48.15; H, 7.11; N, 11.00.

IR $(\nu_{max}^{KBr})$ cm$^{-1}$: 3330($\nu_{NH}$), 2950($\nu_{CH}$), 1750($\nu_{C=O}$), 1680($\nu_{CONH}$).

$^1$H-NMR (CDCl$_3$) δppm:

−0.02    (6H, s, (CH$_3$)$_2$Si—)

0.40–1.16 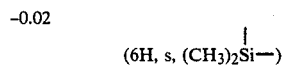
(8H, m, (C<u>H</u>$_3$)$_2$CH—Si—C<u>H</u>$_2$—)

1.32–1.92 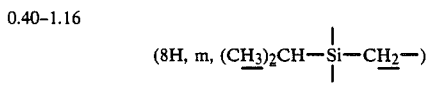
(3H, m, (CH$_3$)$_2$C<u>H</u>—SiCH$_2$C<u>H</u>$_2$—)

2.45–2.92    (4H, m, —CH$_2$SCH$_2$—)

3.63    (2H, q, J=6.5Hz, —NHC<u>H</u>$_2$—)

8.45    (1H, d, J=7.2Hz, C$_6$—H)
9.22    (2H, br., 2 × NH)

Example 13

N-[2-[[3-(t-Butyldimethylsilyl)propyl]thio]ethyl]-5-fluoro-3,4-dihydro-2,4-dioxo-1(2H)-pyrimidinecarboxamide This compound was prepared by the similar procedure as in the case of Example 1, except for treatment with 2-[[3-(butyldimethylsilyl)propyl]thio]ethyl amine (11.7 g, 50.0 mmol) instead of 2-[[3-trimethylsilyl)-propyl]thio]ethyl amine. The crude material was recrystalized from ethyl ether to yield the desired compound (18.4 g, 94.5%).

Melting point: 123°–124° C.

Elementary analysis: $C_{16}H_{28}FN_3O_3SSi$.

Cal.: C, 49.33; H, 7.24; N, 10.79. Found: C, 49.50; H, 7.44; N, 10.72.

IR $(\nu_{max}^{KBr})$ cm$^{-1}$: 3330($\nu_{NH}$), 2850, 2830($\nu_{CH}$), 1735($\nu_{C=O}$), 1680($\nu_{CONH}$).

$^1$H-NMR (CDCl$_3$) δppm:

−0.03    (6H, s, (CH$_3$)$_2$Si—)

0.45–0.82 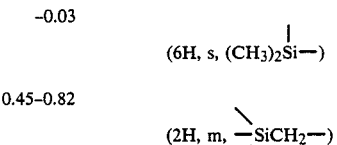
(2H, m, —SiCH$_2$—)

0.89    (9H, s, —C(CH$_3$)$_3$)

1.32–1.92 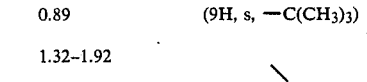
(2H, m, —SiCH$_2$C<u>H</u>$_2$—)

2.45–2.90    (4H, m, —CH$_2$SCH$_2$—)

3.62    (2H, q, J=6.0Hz, —NHC<u>H</u>$_2$—)

8.45    (1H, d, J=7.0Hz, C$_6$—H)
9.22    (2H, br., 2 × NH)

Example 14

N-[3-[[3-(t-Butyldimethylsilyl)propyl]thio]propyl]-5-fluoro-3,4-dihydro-2,4-dioxo-1(2H)-pyrimidinecarboxamide This compound was prepared by the similar procedure as in the case of Example 1, except for treatment with 3-[[3-(t-butyl-dimethylsilyl)propyl]thio]propyl amine (12.4 g, 50.0 mmol) instead of 2-[[3-(trimethylsilyl)propyl]thio]ethyl amine. The crude material was recrystalized from ethyl ether-n-hexane to yield the desired compound (18.4 g, 91.4%).

Melting point: 102°–103° C.

Elementary analysis: $C_{17}H_{30}FN_3O_3SSi$. Cal.: C, 50.59; H, 7.49; N, 10.41. Found: C, 50.34; H, 7.66; N, 10.45.

IR $(\nu_{max}^{KBr})$ cm$^{-1}$: 3350$(\nu_{NH})$, 3080, 2960, 2940, 2860$(\nu_{CH})$, 1730$(\nu_{C=O})$, 1670$(\nu_{CONH})$.

$^1$H-NMR (CDCl$_3$) δppm:

| | |
|---|---|
| −0.09 | (6H, s, —Si(CH$_3$)$_2$) |
| 0.38–0.75 | (2H, m, —CH$_2$Si⟨) |
| 0.85 | (9H, s, —C(CH$_3$)$_3$) |
| 1.25–2.18 | (4H, m, ⟩SiCH$_2$C$\underline{H}_2$CH$_2$SCH$_2$C$\underline{H}_2$—) |
| 2.35–2.75 | (4H, m, ⟩SiCH$_2$CH$_2$C$\underline{H}_2$SC$\underline{H}_2$CH$_2$—) |
| 3.31–3.75 | (2H, m, —C$\underline{H}_2$NH—) |
| 8.50 | (1H, d, J=7.0Hz, C$_6$—H) |
| 9.11 | (1H, br., NH) |

MS (EI/DI) m/z: 216(base peak).

Example 15

N-[3-[[3-(Butyldimethylsilyl)propyl]thio]propyl]-5-fluoro-3,4-dihydro-2,4-dioxo-1(2H)-pyrimidinecarboxamide This compound was prepared by the similar procedure as in the case of Example 1, except for treatment with 3-[[3-(butyldimethylsilyl)propyl]thio]propyl amine (12.4 g, 50.0 mmol) instead of 2-[[3-(trimethylsilyl)propyl]thio]ethyl amine. The crude material was recrystalized from ethyl ether-n-hexane to yield the desired compound (19.3 g, 95.7%).

Melting point: 71°–72° C.

Elementary analysis: $C_{17}H_{30}FN_3O_3SSi$. Cal.: C, 50.59; H, 7.49; N, 10.41. Found: C, 51.10; H, 7.88; N, 10.44.

$^1$H-NMR (CDCl$_3$) δppm:

| | |
|---|---|
| −0.07 | (6H, s, —Si(CH$_3$)$_2$) |
| 0.31–2.21 | (15H, m, —C$\underline{H}_2$C$\underline{H}_2$Si(C$\underline{H}_2$)$_3$C$\underline{H}_3$, —SCH$_2$C$\underline{H}_2$CH$_2$NH—) |
| 2.38–2.75 | (4H, m, ⟩SiCH$_2$CH$_2$C$\underline{H}_2$SC$\underline{H}_2$—) |
| 3.33–3.71 | (2H, m, —C$\underline{H}_2$NH—) |
| 8.46 | (1H, d, J=7.0Hz, C$_6$—H) |
| 9.06 | (1H, br., NH) |

MS (EI/DI) m/z: 258, 216(base peak).

Example 16

N-[3-[[3-(Dimethylphenylsilyl)propyl]thio]propyl]-5-fluoro-3,4-dihydro-2,4-dioxo-1(2H)-pyrimidinecarboxamide This compound was prepared by the similar procedure as in the case of Example 1, except for treatment with 3[[3-(dimethylphenylsilyl)propyl]thio]propyl amine (13.4 g, 50.0 mmol) instead of 2-[[3-(trimethylsilyl)propyl]thio]ethyl amine. The crude material was recrystalized from ethyl ether-n-hexane to yield the desired compound (19.8 g, 93.2%).

Melting point: 51°–52° C.

Elementary analysis: $C_{19}H_{26}FN_3O_3SSi$. Cal.: C, 53.88; H, 6.19; N, 9.92. Found: C, 54.57; H, 6.49; N, 9.79.

IR $(\nu_{max}^{KBr})$ cm$^{-1}$: 3350$(\nu_{NH})$, 3080, 2960, 2930$(\nu_{CH})$, 1735$(\nu_{C=O})$, 1690$(\nu_{CONH})$.

$^1$H-NMR (CDCl$_3$) Δ ppm:

| | |
|---|---|
| 0.22 | (6H, s, Ph(CH$_3$)$_2$Si—) |
| 0.65–1.05 | (2H, m, Ph(CH$_3$)$_2$SiC$\underline{H}_2$—) |
| 1.22–2.08 | (4H, m, Ph(CH$_3$)$_2$SiCH$_2$C$\underline{H}_2$CH$_2$SCH$_2$C$\underline{H}_2$—) |
| 2.35–2.72 | (4H, m, Ph(CH$_3$)$_2$SiCH$_2$CH$_2$C$\underline{H}_2$SC$\underline{H}_2$—) |
| 3.28–3.72 | (2H, m, —C$\underline{H}_2$NH—) |
| 7.18–7.62 | (5H, m, P$\underline{h}$(CH$_3$)$_2$Si—) |
| 8.44 | (1H, d, J=7.0 Hz, C$_6$—H) |
| 9.05 | (2H, br., 2 × NH) |

MS (EI/DI) m/z: 278, 137(base peak).

Example 17

N-[3-[[2-(Butyldimethylsilyl)ethyl]thio]propyl]-5-fluoro-3,4-dihydro-2,4-dioxo-1(2H)-pyrimidinecarboxamide This compound was prepared by the similar procedure as in the case of Example 1, except for treatment with 3-[[2-(butyldimethylsilyl)ethyl]thio]propyl amine (11.7 g, 50.0 mmol) instead of 2-[[3-(trimethylsilyl)propyl]thio]ethyl amine. The crude material was recrystalized from n-propanol to yield the desired compound (11.9 g, 61.2%).

Melting point: 83.5°–84° C.

Elementary analysis: $C_{16}H_{28}FN_3O_3SSi$. Cal.: C, 49.33; H, 7.24; N, 10.79. Found: C, 49.36; H, 7.41; N, 10.87.

IR $(\nu_{max}^{KBr})$ cm$^{-1}$: 3340$(\nu_{NH})$, 3090, 2930$(\nu_{CH})$, 1740$(\nu_{C=O})$, 1690$(\nu_{CONH})$.

$^1$H-NMR (CDCl$_3$) δppm:

| | |
|---|---|
| −0.08 | (6H, s, —Si(CH$_3$)$_2$) |
| 0.2–1.4 | (11H, m, —C$\underline{H}_2$SiCH$_2$CH$_2$CH$_2$CH$_3$) |
| 1.87 | (2H, q, J=7.0Hz, —NCH$_2$C$\underline{H}_2$CH$_2$S—) |
| 2.3–2.9 | (4H, m, —CH$_2$SCH$_2$) |
| 3.47 | (2H, q, J=7.0Hz, —NC$\underline{H}_2$—) |

| 8.48 | (1H, d, J=7.0Hz, $C_6$—H) |
| 8.9-9.3 | (2H, br., NH × 2) |

FAB-MS m/z: 390[(M+1)+].

Example 18

N-[3-[[2-(Dimethylphenylsilyl)ethyl]thio]propyl]-5-fluoro-3,4-dihydro-2,4-dioxo-1(2H)-pyrimidinecarboxamide This compound was prepared by the similar procedure as in the case of Example 1, except for treatment with 3-[[2-(dimethylphenylsilyl)ethyl]thio]propyl amine (12.7 g, 50.0 mmol) instead of 2-[[3-(trimethylsilyl)propyl]thio]ethyl amine. The crude material was recrystalized from ethyl ether to yield the desired compound (15.1 g, 73.7%).

Melting point: 93.5°–94° C.

Elementary analysis: $C_{18}H_{24}FN_3O_3SSi$. Cal.: C, 52.79; H, 5.91; N, 10.26. Found: C, 52.88; H, 6.20; N, 10.37.

IR $(\nu_{max}^{KBr})$ cm$^{-1}$: 3320($\nu_{NH}$), 3060, 2960, 2840($\nu_{CH}$), 1745($\nu_{C=O}$), 1690($\nu_{CONH}$).

$^1$H-NMR (CDCl$_3$) δppm:

| 0.32 | (6H, s, —Si(CH$_3$)$_2$) |
| 0.9–1.3 | 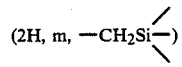 (2H, m, —CH$_2$Si—) |
| 1.90 | (2H, q, J=7.0Hz, —NCH$_2$CH$_2$C$\underline{H_2}$S—) |
| 2.4–2.9 | (4H, m, —CH$_2$SCH$_2$) |
| 3.55 | (2H, q, J=7.0Hz, —NCH$_2$—) |
| 7.3–7.8 | (5H, m, Ar—H) |
| 8.57 | (1H, d, J=7.0Hz, $C_6$—H) |
| 8.9–9.4 | (2H, br., NH × 2) |

FAB-MS m/z: 410[(M+1)+].

PHARMACOLOGICAL TEST EXAMPLE 1

(Suppression of KB cell proliferation in vitro)

In a cultivation device (5% CO$_2$, 37° C.), KB cells (1×10$^4$ cells) were cultivated for 24 hours in a culture tube with 1 ml of Eagle culture medium added 10% ox serum, the used culture medium was thrown away to change with a fresh culture medium (0.9 ml), and then 0.1 ml of a similar culture fluid containing each testing compound prepared by the process as described in the Examples was added to cultivate the same for further 3 days. Thereafter, living cells were dyed with Tripan Blue and measured same through a dye-exclusion method.

A control was treated in a manner similar to the above, except that a culture fluid containing no compound of the invention was added.

50% inhibition density (IC$_{50}$) to the tumor cell proliferation was decided through the tests between the testing group and the control group to obtain results as shown in following Table 1.

TABLE 1

| Compound (Example) | KB IC$_{50}$, μg/ml |
|---|---|
| 1 | 20 |
| 2 | 13 |
| 3 | 12 |
| 4 | 20 |
| 5 | 4 |
| 6 | 12 |
| 7 | 4 |
| 8 | 7 |
| 9 | 15 |
| 10 | 10 |
| 11 | 13 |
| 12 | 15 |
| 13 | 13 |

PHARMACOLOGICAL TEST EXAMPLE 2

(Anti-tumor action to L-1210 leukemia)

L-1210 leukemia cell (1×10$^5$ cells) was transplanted in a abdominal cavity of BDF$_1$ female mice (20–21 g, age of about 5 weeks), and each of testing compounds was orally dosed in 250 mg/kg or 500 mg/kg at 1st, 5th and 9th day after the transplantation to check days of life of the mice. Results are shown in the following Table 2.

$$\text{ILS (\%)} = \frac{T-C}{C} \times 100$$

TABLE 2

| Compound (Example) | Dosage/day × 3 (mg/kg) | L-1210 ILS (%) | Judgement* |
|---|---|---|---|
| 1 | 250 | 28 | + |
|   | 500 | 98 | ++ |
| 2 | 250 | 19 | — |
|   | 500 | 96 | ++ |
| 3 | 250 | 38 | + |
|   | 500 | 82 | ++ |
| 4 | 250 | 12 | — |
|   | 500 | 38 | + |
| 5 | 250 | 51 | + |
|   | 500 | 106 | +++ |
| 6 | 250 | 35 | + |
|   | 500 | 73 | ++ |
| 7 | 250 | 11 | — |
|   | 500 | 11 | — |
| 8 | 250 | 27 | + |
|   | 500 | 70 | ++ |
| 9 | 250 | 45 | + |
|   | 500 | 80 | ++ |
| 10 | 250 | 49 | + |
|   | 500 | 111 | +++ |
| 11 | 250 | 18 | — |
|   | 500 | 81 | ++ |
| 12 | 250 | 24 | — |
|   | 500 | 70 | ++ |
| 13 | 250 | 10 | — |
|   | 500 | 67 | ++ |
| 14 | 250 | 19 | — |
|   | 500 | 68 | ++ |
| 15 | 250 | 26 | + |
|   | 500 | 62 | ++ |
| 16 | 250 | 23 | — |
|   | 500 | 86 | ++ |

*—: 25 > ILS
+: 25 ≦ ILS < 50
++: 50 ≦ ILS < 100
+++: 100 ≦ ILS

PHARMACOLOGICAL TEST EXAMPLE 3

(Anti-tumor action to Colon-38 carcinoma)

0.02 ml of 10(W/V)% cell suspension prepared from a solid cancer cell (Colon-38 carcinoma) were transplanted under skin of $BDF_1$ mice (20–21 g, age of about 5 weeks), and each of testing compounds was orally dosed to the mice at 1st, 5th and 9th day after the transplantation. A major and minor axes of the cancerous tumor were measured at 11th, 14th, 21st, 25th and 28th day after the transplantation to calcurate volume of the tumor in accordance with the following.

$$\tfrac{1}{2} L \times W^2$$

L: major axis (mm)
W: minor axis (mm)

At 28th day from the transplantation, the mice were killed and each of the cancerous tumors was extracted to measure its weight and to determine an inhibition ratio in comparison with a non-treated control group.

Results were shown in following Table 3.

TABLE 3

| Compound (Example) | Dosage/day × 3 (mg/kg) | colon-38 Inhibition ratio (%) |
|---|---|---|
| 1 | 278 | 95.2 |
| 2 | 300 | 71.9 |
| 3 | 315 | 82.1 |
| 4 | 345 | 80.0 |
| 5 | 289 | 89.8 |
| 6 | 300 | 81.2 |
| 7 | 366 | 32.2 |
| 8 | 278 | 78.0 |
| 9 | 338 | 98.4 |
| 10 | 289 | 89.5 |
| 11 | 350 | 90.3 |
| 12 | 338 | 97.3 |
| 13 | 311 | 81.0 |
| 14 | 323 | 90.1 |
| 15 | 323 | 92.3 |
| 16 | 339 | 97.9 |
| 17 | 312 | 97.4 |
| 18 | 328 | 71.3 |

PHARMACOLOGICAL TEST EXAMPLE 4

(Anti-tumor action to MM-46 adenocarcinoma)

MM-46 adenocarcinoma ($1 \times 10^6$ cells) was transplanted under skin of C3H/He female mice (age of about 5 weeks), and each of testing compounds was orally dosed at 1st, 5th and 9th day after the transplantation to check days of life on the mice.

Results were shown in following Table 4.

In the Table,
T: days to death on testing group, and
C: days to death on control group.

TABLE 4

| Compound (Example) | Dosage/day × 3 (mg/kg) | MM-46 adenocarcinoma T/C × 100 (%) |
|---|---|---|
| 1 | 250 | 181 |
| 3 | 250 | 205 |
| 5 | 250 | 162 |

PHARMACOLOGICAL TEST EXAMPLE 5

(Anti-tumor action to B-16 melanoma)

B-16 melanoma ($1 \times 10^5$ cells) was transplanted under skin of $BDF_1$ female mice (age of about 5 weeks), and each of testing compounds was orally dosed at 1st, 5th and 9th day after the transplantation. At 21st day after the transplantation, the mice were killed to measure a weight of the cancerous tumor and to finally determine an inhibition ratio.

Results were shown in following Table 5.

TABLE 5

| Compound (Example) | Dosage/day × 3 mg/kg | B-16 melanoma Inhibition ratio (%) |
|---|---|---|
| 1 | 250 | 73.8 |
|   | 125 | 25.8 |
| 2 | 300 | 47.2 |
| 3 | 300 | 62.0 |
| 5 | 300 | 79.7 |
| 6 | 300 | 53.5 |
| 8 | 250 | 4.3 |
| 9 | 250 | 19.4 |
|   | 125 | 17.6 |
| 10 | 250 | 15.2 |
|   | 125 | 38.1 |
| 11 | 250 | 45.7 |
|   | 125 | 32.8 |
| 12 | 250 | 37.9 |
|   | 125 | 34.2 |
| 13 | 250 | 43.1 |
|   | 125 | 38.0 |
| 14 | 250 | 46.3 |
|   | 125 | 55.2 |
| 15 | 250 | 88.5 |
|   | 125 | 69.5 |
| 16 | 250 | 70.5 |
|   | 125 | 82.2 |
| 17 | 400 | 34.8 |
|   | 200 | 16.3 |
|   | 100 | 54.3 |
| 18 | 400 | 29.6 |
|   | 200 | 46.7 |
|   | 100 | 55.2 |

PHARMACOLOGICAL TEST EXAMPLE 6

(Anti-tumor action to Lewis lung carcinoma)

Lewis lung carcinoma ($1 \times 10^5$ cells) was transplanted under skin of right ear of $BDF_1$ mice (age of about 5 weeks), and each of testing compounds was orally dosed 10 times from 1st to 10th day after the transplantation. At 21st day after the transplantation, the mice were killed to measure a weight of the primarly tumor and to extract a lung. The lung was fixed in a conventional manner to count a number of metastasis on cancerous cells with use of a stereomicroscope having a low magnification. An anti-tumor action of each compound was expressed with an inhibition in weight of the primarly tumor and an inhibition of the metastasis.

Results were shown in following Table 6.

TABLE 6

| Compound (Example) | Dosage/day × 10 (mg/kg) | Inhibition Ratio weight LLC (%) | metastasis (%) |
|---|---|---|---|
| 1 | 13 | 0.0 | 50.9 |
|   | 13 + Amputation | 33.2 | (26.6) |
|   | 26 + Amputation | 59.8 | (>63.0) |
|   | 26 | 51.1 | 79.2 |
|   | 52 | 31.1 | 95.7 |
| 2 | 14 | 0.0 | 45.2 |
| 3 | 29.5 | 20.7 | 57.5 |
|   | 59 | 0.0 | 95.1 |
| 4 | 32 | 4.6 | 76.2 |
|   | 64 | 18.0 | 97.5 |
| 5 | 13.5 | 0.0 | 19.3 |
|   | 13.5 + Amputation | 34.7 | (15.4) |
|   | 27 + Amputation | 35.8 | (>39.5) |
|   | 27 | 7.1 | 78.4 |
|   | 54 | 34.9 | 83.0 |
| 6 | 13.5 + Amputation | 37.3 | (18.3) |

TABLE 6-continued

| Compound (Example) | Dosage/day × 10 (mg/kg) | Inhibition Ratio weight LLC (%) | metastasis (%) |
|---|---|---|---|
| | 27 + Amputation | 30.9 | (23.1) |
| | 27 | 39.6 | 92.6 |
| | 54 | 38.0 | 95.1 |
| 7 | 34 | 31.0 | 67.1 |
| | 68 | 25.0 | 87.7 |
| 8 | 13 | 0.0 | 53.0 |
| | 13 + Amputation | 33.3 | (18.4) |
| | 26 | 26.2 | 92.5 |
| | 26 + Amputation | 64.9 | (33.6) |

PHARMACOLOGICAL TEST EXAMPLE 7

(Acute toxicity)

Each of testing compounds suspended in 0.1% P-1570 was orally and forcedly dosed through a gastric probe to CrJ/CDI female mice (21 to 22 g, age of about 5 weeks). An identification number was given to each mouse, and a weighing and observation on general behavior were carried out just before the dosage and each day after the same. Each of died mice was subjected without delay to an autopsy to check the same, more particularly in detail on enterona. All of living mice were killed at 21st day from the dosage to carry out an autopsy for checking the same, more particularly on entrails.

An $LD_{50}$ was calculated in accordance with the Leed and Munch's method.

A similar test was carried out on each controls of 1-[2-[(2-trimethylsilylethyl)thio]ethylcarbamoyl]-5-fluorouracil and 1-hexylcarbamoyl-5-fluorouracil (HCFU) which is one of exemplary anti-tumor agents. On the former control compound, a spasm was observed in some mice and an opinion on autopsy of the concerned mice showed an ulcer and laxative feces, none of which was recognized through an autopsy for the mice having dosed the compound according to the invention.

Results were shown in following Table 7.

TABLE 7

| Compounds | $LD_{50}$ (mg/kg) |
|---|---|
| Examples | |
| 1 | 1575 |
| 2 | 1545 |
| 3 | 1500 |
| 4 | 1580 |
| 5 | 1380 |
| 6 | 1385 |
| 7 | 1400 |
| 8 | 1355 |
| 9 | 2250 |
| 10 | 2170 |
| 11 | 2120 |
| 13 | 1380 |
| 14 | 1800 |
| 15 | 1850 |
| 16 | 1800 |
| Controls | |
| 1-[2-[(2-trimethylsilylethyl)thio]-ethylcarbamoyl]-5-fluorouracil | 1095 |
| HCFU | 1250 |

PRESCRIPTIONAL EXAMPLE 1

(Tablet)

Following components were mixed to prepare tablets in a conventional manner.

| Compound of Example 1 | 100 (mg) |
|---|---|
| Crystalline cellulose | 20 |
| Lactose | 41 |
| Corn starch | 30 |
| Hydroxypropylcellulose | 6 |
| Magnesium stearate | 3 |
| | 200 mg/tablet |

PRESCRIPTIONAL EXAMPLE 2

(Capsule)

Following components were mixed and charged in capsules in a conventional manner to prepare capsuled pharmaceutical agents.

| Compound of Example 5 | 200 (mg) |
|---|---|
| Crystalline cellulose | 50 |
| Silicic anhydride | 2 |
| Magnesium stearate | 3 |
| | 255 mg/capsule |

PRESCRIPTIONAL EXAMPLE 3

(Granule)

Following components were mixed and packed in a conventional manner to prepare granular pharmaceutical agents.

| Compound of Example 8 | 500 (mg) |
|---|---|
| Lactose | 323 |
| Corn starch | 150 |
| Polyvinylpyrrolidone | 25 |
| Silicic anhydride | 2 |
| | 1000 mg/package |

PRESCRIPTIONAL EXAMPLE 4

(Suppository)

Following components were mixed to prepare suppositories in a conventional manner.

| Compound of Example 10 | 300 (mg) |
|---|---|
| Witep-Sol W-35 | 1700 |
| | 2000 mg/suppository |

We claim:

1. A novel organo-silicone compound represented by the formula

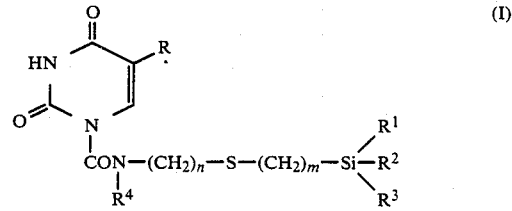

wherein R is fluorine, $R^1$, $R^2$ and $R^3$ are an alkyl group of 1 to 10 carbon atoms, or a phenyl radical, respectively, $R^4$ is hydrogen, and m and n are an integer of 2 or 3, but those do not represent same integer of 2, when all of $R^1$, $R^2$ and $R^3$ represents methyl radical.

2. A compound as claimed in claim 1, wherein $R^1$, $R^2$ and $R^3$ are methyl radical, respectively, m is an integer of 3, and n is an integer of 2.

3. A compound as claimed in claim 1, wherein $R^1$, $R^2$ and $R^3$ are ethyl radical, respectively, and m and n are an integer of 2, respectively.

4. A compound as claimed in claim 1, wherein $R^1$ and $R^2$ are methyl radical, respectively, $R^3$ is phenyl radical, and m and n are integer of 2, respectively.

5. A compound as claimed in claim 1, wherein $R^1$ and $R^2$ are methyl radical, respectively, $R^3$ is n-octyl radical, and m and n are an integer of 2, respectively.

6. A compound as claimed in claim 1, wherein $R^1$ and $R^2$ are methyl radical, respectively, $R^3$ is isopropyl radical, and m and n are an integer of 2, respectively.

7. A compound as claimed in claim 1, wherein $R^1$ and $R^2$ are methyl radical, respectively, $R^3$ is n-butyl radical, and m and n are integer of 2, respectively.

8. A compound as claimed in claim 1, wherein $R^1$ is methyl radical, $R^2$ and $R^3$ are phenyl radical, respectively, and m and n are an integer of 2, respectively.

9. A compound as claimed in clkaim 1, wherein $R^1$, $R^2$ and $R^3$ are methyl radical, respectively, m is an integer of 2, and n is an integer of 3.

10. A compound as claimed in claim 1, wherein $R^1$ and $R^2$ are methyl radical, respectively, $R^3$ is isopropyl radical, m is an integer of 2, and n is an integer of 3.

11. A compound as claimed in claim 1, wherein $R^1$, $R^2$ and $R^3$ are methyl radical, respectively, and m and n are an integer of 3, respectively.

12. A compound as claimed in claim 1, wherein $R^1$ and $R^2$ are methyl radical, respectively, $R^3$ is isopropyl radical, and m and n are an integer of 3, respectively.

13. A compound as claimed in claim 1, wherein $R^1$ and $R^2$ are methyl radical, respectively, $R^3$ is isopropyl radical, m is an integer of 3, and n is an integer of 2.

14. A compound as claimed in claim 1, wherein $R^1$ and $R^2$ are methyl radical, respectively, $R^3$ is t-butyl radical, m is an integer of 3, and n is an integer of 2.

15. A compound as claimed in claim 1, wherein $R^1$ and $R^2$ are methyl radical, respectively, $R^3$ is t-butyl radical, and m and n are an integer of 3, respectively.

16. A compound as claimed in claim 1, wherein $R^1$ and $R^2$ are methyl radical, respectively, $R^3$ is n-butyl radical, and m and n are an integer of 3, respectively.

17. A compound as claimed in claim 1, wherein $R^1$ and $R^2$ are methyl radical, respectively, $R^3$ is phenyl radical, and m and n are an integer of 3, respectively.

18. A compound as claimed in claim 1, wherein $R^1$ and $R^2$ are methyl radical, respectively, $R^3$ is n-butyl radical, m is an integer of 2, and n is an integer of 3.

19. A compound as claimed in claim 1, wherein $R^1$ and $R^2$ are methyl radical, respectively, $R^3$ is phenyl radical, m is an integer of 2, and n is an integer of 3.

20. An anti-tumor agent which comprises as an effective component, at least one organo-silicone compound represented by the formula

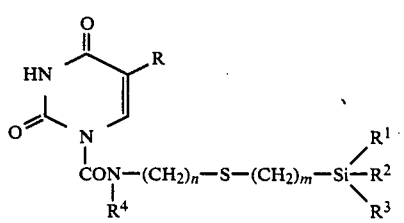

(I)

wherein R is fluorine, $R^1$, $R^2$ and $R^3$ are an alkyl group of 1 to 10 carbon atoms, or a phenyl radical, respectively, $R^4$ is hydrogen and m and n are an integer of 2 or 3, but those do not represent same integer of 2, when all of $R^1$, $R^2$ and $R^3$ represents methyl radical; together with a pharmaceutically acceptable carrier.

21. An anti-tumor agent as claimed in claim 20, characterized in that the effective component is a compound represented by the formula, wherein $R^1$, $R^2$ and $R^3$ are methyl radical, respectively, m is an integer of 3, and n is an integer of 2.

22. An anti-tumor agent as claimed in claim 20, characterized in that the effective component is a compound represented by the formula, wherein $R^1$, $R^2$ and $R^3$ are ethyl radical, respectively, and m and n are an integer of 2, respectively.

23. An anti-tumor agent as claimed in claim 20, characterized in that the effective component is a compound represented by the formula, wherein $R^1$ and $R^2$ are methyl radical, respectively, $R^3$ is phenyl radical, and m and n are an integer of 2, respectively.

24. An anti-tumor agent as claimed in claim 20, characterized in that the effective component is a compound represented by the formula, wherein $R^1$ and $R^2$ are methyl radical, respectively, $R^3$ is n-octyl radical, and m and n are an integer of 2, respectively.

25. An anti-tumor agent as claimed in claim 20, characterized in that the effective component is a compound represented by the formula, wherein $R^1$ and $R^2$ are methyl radical, respectively, $R^3$ is isopropyl radical, and m and n are an integer of 2, respectively.

26. An anti-tumor agent as claimed in claim 20, characterized in that the effective component is a compound represented by the formula, wherein $R^1$ and $R^2$ are methyl radical, respectively, $R^3$ is n-butyl radical, and m and n are an integer of 2, respectively.

27. An anti-tumor agent as claimed in claim 20, characterized in that the effective component is a compound represented by the formula, wherein $R^1$ is methyl radical, $R^2$ and $R^3$ are phenyl radical, respectively, and m and n are an integer of 2, respectively.

28. An anti-tumor agent as claimed in claim 20, characterized in that the effective component is a compound represented by the formula, wherein $R^1$, $R^2$ and $R^3$ are methyl radical, respectively, m is an integer of 2, and an is an integer of 3.

29. An anti-tumor agent as claimed in claim 20, characterized in that the effective component is a compound represented by the formula, wherein $R^1$ and $R^2$ are methyl radical, respectively, $R^3$ is isopropyl radical, m is an integer of 2, and n is an integer of 3.

30. An anti-tumor agent as claimed in claim 20, characterized in that the effective component is a compound represented by the formula, wherein $R^1$, $R^2$ and $R^3$ are methyl radical, respectively, and m and n are an integer of 3, respectively.

31. An anti-tumor agent as claimed in claim 20, characterized in that the effective component is a compound represented by the formula, wherein $R^1$ and $R^2$ are methyl radical, respectively, $R^3$ is isopropyl radical, and m and n are an integer of 3, respectively.

32. An anti-tumor agent as claimed in claim 20, characterized in that the effective component is a compound represented by the formula, wherein $R^1$ and $R^2$ are methyl radical, respectively, $R^3$ is isopropyl radical, m is an integer of 3, and n is an integer of 2.

33. An anti-tumor agent as claimed in claim 20, characterized in that the effective component is a compound represented by the formula, wherein $R^1$ and $R^2$ are methyl radical, respectively, $R^3$ is t-butyl radical, m is an integer of 3, and n is an integer of 2.

34. An anti-tumor agent as claimed in claim 20, characterized in that the effective component is a compound represented by the formula, wherein $R^1$ and $R^2$ are methyl radical, respectively, $R^3$ is t-butyl radical, and m and n are an integer of 3, respectively.

35. An anti-tumor agent as claimed in claim 20, characterized in that the effective component is a compound represented by the formula, wherein $R^1$ and $R^2$ are methyl radical, respectively, $R^3$ is n-butyl radical, and m and n are an integer of 3, respectively.

36. An anti-tumor agent as claimed in claim 20, characterized in that the effective component is a compound represented by the formula, wherein $R^1$ and $R^2$ are methyl radical, respectively, $R^3$ is phenyl radical, and m and n are an integer of 3, respectively.

37. An anti-tumor agent as claimed in claim 20, characterized in that the effective component is a compound represented by the formula, wherein $R^1$ and $R^2$ are methyl radical, respectively, $R^3$ is n-butyl radical, m is an integer of 2, and n is an integer of 3.

38. An anti-tumor agent as claimed in claim 20, characterized in that the effective component is a compound represented by the formula, wherein $R^1$ and $R^2$ are methyl radical, respectively, $R^3$ is phenyl radical, m is an integer of 2, and n is an integer of 3.

* * * * *

UNITED STATES PATENT AND TRADEMARK OFFICE
CERTIFICATE OF CORRECTION

PATENT NO. : 4,778,797
DATED : October 18, 1988
INVENTOR(S) : Shigeshi TOYOSHIMA et al It is certified that error appears in the above-identified patent and that said Letters Patent is hereby corrected as shown below:

On the cover page, Item [75], after "Koichi Ito, Tokyo", insert --; Toshinobu Ishihara, Niigata; Akira Yamamoto, Niigata--.

Signed and Sealed this

Second Day of May, 1989

*Attest:*

DONALD J. QUIGG

*Attesting Officer*    *Commissioner of Patents and Trademarks*